United States Patent
Riggs

(10) Patent No.: US 9,157,095 B2
(45) Date of Patent: Oct. 13, 2015

(54) GENETICALLY MODIFIED SEED COMBINED WITH SPORE FORMING BACTERIUM AND OPTICAL INSECT CONTROL AGENTS AND METHODS FOR TREATING PLANTS

(75) Inventor: Jennifer Riggs, Raleigh, NC (US)

(73) Assignee: Bayer CropScience LP, Research Triangle Park, NC (US)

( * ) Notice: Subject to any disclaimer, the term of this patent is extended or adjusted under 35 U.S.C. 154(b) by 322 days.

(21) Appl. No.: 13/059,124

(22) PCT Filed: Sep. 3, 2009

(86) PCT No.: PCT/US2009/055842
§ 371 (c)(1),
(2), (4) Date: Mar. 2, 2011

(87) PCT Pub. No.: WO2010/030554
PCT Pub. Date: Mar. 18, 2010

(65) Prior Publication Data
US 2011/0154544 A1    Jun. 23, 2011

Related U.S. Application Data

(60) Provisional application No. 61/191,620, filed on Sep. 10, 2008.

(51) Int. Cl.
*A01N 63/00* (2006.01)
*C12N 15/82* (2006.01)

(52) U.S. Cl.
CPC ............ *C12N 15/8275* (2013.01); *A01N 63/00* (2013.01); *C12N 15/8286* (2013.01)

(58) Field of Classification Search
None
See application file for complete search history.

(56) References Cited

U.S. PATENT DOCUMENTS

| | | | | |
|---|---|---|---|---|
| 6,156,699 | A * | 12/2000 | Johnson et al. | 504/100 |
| 6,406,690 | B1 * | 6/2002 | Peleg et al. | 424/93.46 |
| 2004/0023802 | A1 * | 2/2004 | Asrar et al. | 504/100 |

OTHER PUBLICATIONS

Cornell University PMEP. 1985. Pesticide Management Education Program. NEMACUR Chemical Profile. 2 pages.*
Ranked listing of biological control agents for genome sequencing. 2003. Ohio Agriculture Research and Development Center (OARDC). pp. 1-3.*
Tian et al. 2007. Bacteria used in the biological control of plant-parasitic nematodes: populations, mechanisms of action, and future prospects. FEMS Microbiol. Ecol. 61:197-213.*
Carneiro et al. 1998. Nematicidal activity of *Bacillus sp.* strains on juveniles of *Meloidogyne javanica*. Nematologia Brasileira. 22(1):12-21.*
Riggs et al. Insect control spectrum of AERIS: A Seed Treatment System. Jan. 12, 2007. Poster Abstract from Jan. 9-12, 2007 Beltwide Cotton Conferences.*
Tian, Baoyu, "Bacteria used in the biological control of plant-parasitic nematodes: populations, mechanisms of action, and future prospects", FEMS Microbiol Ecol, vol. 61, pp. 197-213, 2007.
OARDC, "Ranked Listing of Microbial Biological Control Agents to be Included on the APS Microbial Genome Sequencing Priority List", Jun. 3, 3002, [online], <URL: http://www.oardc.ohio-state.edu/apsbcc/MicSeqProposal.htm>. Especially p. 2 Recommeded List.
International Search Report for PCT/US09/55842 Oct. 21, 2009.

* cited by examiner

*Primary Examiner* — David T Fox
*Assistant Examiner* — Jared Shapiro

(57) ABSTRACT

Products are provided that improve overall plant vigor and yield by combining agriculturally effective amounts of at least one spore-forming bacterium and at least one optional insect control agent to a genetically modified plant, plant part, or seed. This product is particularly effective in the presence of plant parasitic nematode and fungal species. Use of the product leads to an overall reduction in crop losses caused by either plant parasitic nematodes or fungi and this reduction is much greater than using genetically modified seed with just an insect control agent. According to some embodiments, the use of the product results in about a 2%-10% increase in soybean bushel yield, 3%-6.5% increase in cotton yield, and 3%-8% in corn bushel yield. Methods for utilizing and manufacturing the combination are also provided.

16 Claims, No Drawings

GENETICALLY MODIFIED SEED COMBINED WITH SPORE FORMING BACTERIUM AND OPTICAL INSECT CONTROL AGENTS AND METHODS FOR TREATING PLANTS

BACKGROUND OF THE INVENTION

1. Field of the Invention

The invention relates generally to products and methods for reducing overall damage and losses in plant health, vigor, and yield caused by plant parasitic nematode and fungi. More specifically, the invention relates to products comprising genetically modified seed and at least one agriculturally beneficial spore-forming bacterium combined with an optional insect control agent, and methods for utilizing the combination for treating genetically modified seeds, plants and plant parts.

2. Description of Related Art

Nematodes are microscopic unsegmented worms known to reside in virtually every type of environment (terrestrial, freshwater, marine). Of the over 80,000 known species, many are agriculturally significant, particularly those classified as pests. One such species is the root knot nematode which attacks a broad range of plants, shrubs, and crops. These soil-born nematodes attack newly formed roots causing stunted growth, swelling or gall formation. The roots may then crack open thus exposing the roots to other microorganisms such as bacteria and fungi. With environmentally friendly practices such as reduced or no tillage farming, and various nematode species acquiring resistance to transgenic seed, nematode related crop losses appear to be on the rise.

Chemical nematicides such as soil fumigants or non-fumigants have been in use for many years to combat infestations. Such nematicides may require repeated applications of synthetic chemicals to the ground prior to planting. Due to their toxicity, chemical nematicides have come under scrutiny from the Environmental Protection Agency (EPA) and in some cases their use has been limited or restricted by the EPA. As the use of traditional chemical nematicides such as methyl-bromide and organophosphates continue to be phased out, a need for the development of alternative treatment options has arisen. U.S. Pat. No. 6,593,273 discloses treatment of transgenic corn seeds with pesticides to treat nematode infestations.

U.S. Pat. No. 6,844,339 discloses using a neonicotinoid to control nematodes. The preferred compounds in the '339 patent are nitroimino or nitroguanidino compounds. The neonicotinoid can be applied to either the nematode environment or plant material itself. WO/2007/149817 discloses combining a biological control agent with a nematicide, such as avermectin, to enhance plant protection against pests and pathogens. This combination, however, does not address the toxicity of using certain chemical nematicides.

SUMMARY OF THE INVENTION

There remains a need for effective compositions and methods that use environmentally friendly biological components and less toxic chemical nematicides, but utilize them in such a manner that they can provide improved plant vigor and yield without the use of more toxic traditional chemical nematicides.

The invention provides improved products and methods for controlling nematode damage or infestations. The product uses at least one spore forming bacterium and an optional insect control agent an optional fungicide control agent in combination with a genetically modified seed, plant, or plant part.

Methods for treating a seed, plant and/or plant part are also provided. The method comprises (a) providing a composition comprising an effective amount of at least one spore-forming bacterium; (b) combining the spore-forming bacterium with an optional insect control agent; and (c) applying the composition to the genetically modified seed, plant, and/or plant part. Application can be done in any desired manner, such as in the form of seed coating, soil drench, and/or directly in-furrow and/or as a foliar spray and applied either pre-emergence, post-emergence or both. Optionally, the insect control agent can be applied separately to the genetically modified seed, plant, or plant part. Further, at least one fungicide may also be combined with the spore-forming bacterium, optional insect control agent, or applied separately to the genetically modified plant, seed, or plant part. In sum, the individual components or composition can be applied to the seed, the plant, the plant foliar, to the fruit of the plant, or the soil wherein the plant is growing or wherein it is desired to grow.

According to one aspect of the invention, a product is provided comprising a spore-forming bacterium combined with an optional insect control agent and a genetically modified seed.

In another aspect of the invention, a method of treating a genetically modified seed, plant, or plant part is provided, comprising applying to the seed, plant or plant part at least one spore-forming bacterium; and, optionally, at least one insect control agent.

In a further aspect of the invention, a method of protecting a genetically modified seed, plant, or plant part from nematodes is provided, comprising providing at least one composition comprising 0.0001 to 20% by weight of at least one spore-forming bacterium and 0.001 to 20% by weight of at least one insect control agent; and applying the composition to the seed, plant, or plant part.

In yet another aspect of the invention, a composition for protecting a genetically modified seed, plant, or plant part from nematodes is provided, comprising: (i) at least one spore-forming bacterium in an amount of from about 2% by weight to 80% by weight; (ii) at least one insect control agent in an amount of from about 1% by weight to about 80% by weight; and (iii) a solvent.

In yet a further aspect of the invention, a method of manufacturing a genetically modified seed treated with at least one spore-forming bacteria and an optional insect control agent is provided, comprising: (i) applying said spore-forming bacteria and optional insect control agent to said genetically modified seed; and (ii) mixing said genetically modified seed to achieve a substantially uniform treatment.

Other products and methods in accordance with the composition are provided in the detailed description and claims that follow below. Additional objects, features, and advantages will be sent forth in the description that follows, and in part, will be obvious from the description, or may be learned by practice of the invention. The objects, features, and advantages may be realized and obtained by means of the instrumentalities and combination particularly pointed out in the appended claims.

DETAILED DESCRIPTION OF THE INVENTION

The products disclosed herein have been found to provide a greater degree of plant vigor and yield in nematode infested environments than would be expected from the application of insecticides to genetically modified seeds, plants, and plant parts. At least some of the optional insect control agents have been shown to provide increased root mass even in the absence of insect pressure which increased root mass leads to improved establishment of the beneficial bacteria within the rhizosphere which, in turn, reduces overall losses in crop vigor and yields caused by either plant parasitic nematodes or fungi. Along with the physical combination of these components while treating plants and plant parts, the compositions may be formulated to provide a stable environment for living spore-forming bacteriums such as spore-forming, root-colonizing bacteria. Various additives, such as fungicides, insecticides, stabilizers, emulsifiers, may be added to the spore-forming bacterium and/or genetically modified seed, plant, or plant part depending on the desired properties.

The genetically modified seeds, plants, or plant parts are typically developed for insect control and herbicide tolerance. Thus, the addition of utilizing a spore forming bacterium with the optional insect control agent helps complete the ability of the seed to survive under adverse conditions. The at least one spore-forming bacterium generally has proven agriculturally beneficial to colonize a plant's root system. The optional insect control agent can be at least one chemical insecticide that, whether or not having proven direct nematicidal or fungicidal activity, does possess the proven ability to increase the mass of the plant's root system to which it is applied. The genetically modified seed can be any seed that results in a genetically modified plant or plant part that expresses insect toxins or herbicide resistance. Further, the genetically modified seed can be any seed that results in a genetically modified plant or plant part that expresses toxins or resistance to bacterial and fungi. Moreover, the genetically modified seed may be any seed that results in a genetically modified plant or plant part that expresses tolerance to environmental factors such as water stress and nitrogen production.

Regarding insect toxins, U.S. Pat. No. 5,877,012, herein incorporated by reference in its entirety, discloses the cloning and expression of proteins from such organisms as *Bacillus, Pseudomonas, Clavibacter*, and *Rhizobium* into plants to obtain transgenic plants with resistance to such pests as black cutworms, armyworms, and borers. Further, U.S. Pat. Nos. 5,625,136 and 5,859,336, hereby incorporated by reference in their entirety, disclose transforming corn plants with a gene from *B. thuringiensis* that encodes for delta-endotoxins proving the transgenic corn with improved resistance to European corn borers. A comprehensive report of field trials of transgenic corn that expresses an insecticidal protein from *B. thuringiensis* has been provided by Armstrong et al., in *Crop Science*, 35(2):550-557 (1995), hereby incorporated by reference in its entirety. Additional references that disclose corn encoded with the *B. thuringiensis* gene, include U.S. Pat. Nos. 4,766,203; 4,797,279; and 4,910,016, hereby incorporated by reference in their entirety; and WO 99/312248, hereby incorporated by reference in its entirety. Regarding herbicide resistance, U.S. Pat. No. 4,971,908, herein incorporated by reference in its entirety, discloses genetically modified plants that are glyphosate resistant. Glyphosate resistance is achieved by genetically modifying the plant or seed to produce mutant EPSP synthase enzymes that exhibit a lower affinity for glyphosate while maintaining catalytic activity. Additional references that disclose glyphosate resistant plants and seeds include U.S. Pat. Nos. 5,463,175; 5,776,760; 5,804,425; 6,689,880; 6,803,501; 7,214,535; and 7,335,816, herein incorporated by reference in their entirety.

The one spore-forming bacterium has demonstrated agriculture benefit. Preferably, the at least one spore-forming bacteria is a root colonizing bacterium (e.g. rhizobacterium).

Agriculture benefit refers to the bacterium's ability to provide protection from the harmful effects of plant pathogenic fungi or bacteria and/or soil born animals such as those belonging to the phylum Nematoda or Aschelminthes. Protection against plant parasitic nematodes and parasitic microorganisms can occur through chitinolytic, proteolytic, collagenolytic, or other activities detrimental to these soil born animals and/or detrimental to microbial populations. Bacteria exhibiting these nematicidal, fungicidal and bactericidal properties may include but are not limited to, *Bacillus argri, Bacillus aizawai, Bacillus albolactis, Bacillus amyloliquefaciens, Bacillus cereus, Bacillus coagulans, Bacillus endoparasiticus, Bacillus endorhythmos, Bacillus firmus, Bacillus kurstaki, Bacillus lacticola, Bacillus lactimorbus, Bacillus lactis, Bacillus laterosporus, Bacillus lentimorbus, Bacillus licheniformis, Bacillus megaterium, Bacillus medusa, Bacillus metiens, Bacillus natto, Bacillus nigrificans, Bacillus popillae, Bacillus pumilus, Bacillus siamensis, Bacillus sphearicus, Bacillus* spp., *Bacillus subtilis, Bacillus thurngiensis, Bacillus unifagellatus*, plus those listed in the category of *Bacillus* Genus in *Bergey's Manual of Systematic Bacteriology*, First Ed. (1986), hereby incorporated by reference in its entirety.

Preferably, the spore-forming bacterium is at least one *B. firmus* CNCM I-1582 spore and/or *B. cereus* strain CNCM I-1562 spore as disclosed in U.S. Pat. No. 6,406,690, hereby incorporated by reference in its entirety. Most preferably, the spore-forming bacterium is *B. firmus* CNCM I-1582. Alternatively, the spore-forming bacterium can be at least one *B. amyloliquefaciens* IN937a, at least one *Bacillus subtillis* strain designated GB03, or at least one *B. pumulis* strain designated GB34. Further, the spore-forming bacterium can be a mixture of any species listed above, as well as other spore-forming, root colonizing bacteria known to exhibit agriculturally beneficial properties.

In a preferred embodiment, the spore-forming bacterium can be applied to the seed, plant, or plant parts as either a powder, aqueous, or non-aqueous solution. Powders can be either dry, wettable powders, or water dispersable granules. Preferably, the spore-forming bacterium is a solution, emulsifiable concentrate, wettable powder, suspension concentrate, soluble powder, granules, suspension-emulsion concentrate, natural and synthetic materials impregnated with active compounds, and fine control release capsules. The spore-forming bacterium in a liquid or dry form may be admixed with the soil prior to, at the time of, or after planting. Most preferably, the formulation is in a liquid state admixed with the soil prior to or at the time of planting.

The amount of the at least one spore-forming bacterium employed in the compositions can vary depending on the final formulation as well as size or type of the plant, plant part, or seed to be utilized. Preferably, at least one spore-forming bacterium in the compositions is present in about 2% by weight of total formulation to about 80% by weight of total formulation. More preferably, about 5% by weight of total formulation to about 65% by weight of total formulation; and most preferably about 10% by weight of total formulation to about 60% by weight of total formulation.

The compositions further comprise at least one optional insect control agent. Preferably, the insect control agent can be any insecticidal chemical compound or composition having insecticidal activity, but no direct nematicidal activity and no detrimental activity against the utilized spore-forming bacterium, and preferably also has the added ability to increase root mass upon application. Alternatively, the combination may comprise at least one additional chemical compound that does exhibit nematicidal or fungicidal properties. Such compositions can by useful in geographical areas having extremely high populations of nematode infestation or to provide additional fungicidal activity against heavy fungal disease pressure. The plant, seed, or plant material can be treated separately or simultaneously with the additional insect or fungicidal control agent. Most preferably, the insect control agent is a non-nematicidal neonicotinoid insecticide compound of formula (I)

In another preferred embodiment, the optional insect control agent is at least one systemic, non-nematicidal neonicotinoid insecticide compound of formula (I)

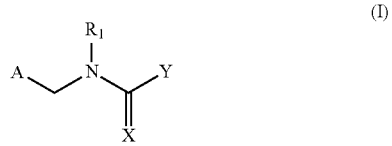

(I)

wherein

A is 2-chloropyrid-5-yl, 2-methylpyrid-5-yl, 1-oxido-3-pyridinio, 2-chloro-1-oxido-5-pyridinio, 2,3-dichloro-1-oxido-5-pyridinio, tetrahydrofuran-3-yl, 5-methyl-tetrahydrofuran-3-yl or 2-chlorothiazol-5-yl group;

R is hydrogen, $C_1$-$C_6$ alkyl, phenyl-$C_1$-$C_4$ alkyl, $C_3$-$C_6$ cycloalkyl, $C_2$-$C_6$ alkenyl or $C_2$-$C_6$ alkynyl;

Y is —N(R)($R_2$) or $SR_2$;

$R_1$ and $R_2$ are independently of each other $C_1$-$C_4$-alkyl, $C_1$-$C_4$-alkenyl, $C_1$-$C_4$-alkinyl, —C(=O)—$CH_3$ or benzyl; or together form a group —$CH_2$—$CH_2$—, —$CH_2$—$CH_2$—$CH_2$—, —$CH_2$—O—$CH_2$—, —$CH_2$—S—$CH_2$—, —$CH_2$—NH—$CH_2$— or —$CH_2$—N($CH_3$)—$CH_2$—; and X is N—$NO_2$ or N—CN or CH—$NO_2$.

Particularly preferred non-nematicidal, neonicotinoid insecticides include 1-(6-chloro-3-pyridylmethyl)-N-nitroimidazolidin-2-ylideneamine (imidacloprid), 3-(6-chloro-3-pyridylmethyl)-1,3-thiazolidin-2-ylidenecyanamide (thiacloprid), 1-(2-chloro-1,3-thiazol-5-ylmethyl)-3-methyl-2-nitroguanidine (clothianidin), nitempyran, $N^1$-[(6-chloro-3-pyridyl)methyl]-$N^2$-cyano-$N^1$-methylacetamidine (acetamiprid), 3-(2-chloro-1,3-thiazol-5-ylmethyl)-5-methyl-1,3,5-oxadiazinan-4-ylidene(nitro)amine (thiamethoxam) and 1-methyl-2-nitro-3-(tetrahydro-3-furylmethyl)guanidine (dinotefuran).

In an alternative embodiment, the spore-forming bacterium-insect control agent combination can optionally include an additional chemical compound with direct nematicidal activity. Suitable nematicidal insect control agents include antibiotic nematicides such as abamectin; carbamate nematicides such as benomyl, carbofuran, carbosulfan, and cleothocard; oxime carbamate nematicides such as alanycarb, aldicarb, aldoxycarb, oxamyl; organophosphorous nematicides such as diamidafos, fenamiphos, fosthietan, phosphamidon, cadusafos, chlorpyrifos, diclofenthion, dimethoate, ethoprophos, fensulfothion, fostiazate, heterophos, isamidofos, isazofos, methomyl, phorate, phosphocarb, terbufos, thiodicarb, thionazin, triazophos, imicyafos, and mecarphon. Other suitable nematicidal insect control agents include acetoprole, benclothiaz, chloropicrin, dazomet, DBCP, DCIP, 1,2-dichloropropane, 1,3-dichloropropene, furfural, iodomethane, metam, methyl bromide, methyl isothiocyanate, and xylenols. Alternatively, the spore-forming bacterium can also be combined with biological nematicide agents such as *Myrothecium verrucaria, Burholderia cepacia, Bacillus chitonosporus* and *Paecilomyces lilacinus* or nematicidal agents of plant or animal origin such as harpin proteins, amino acid sequences or virus, viroid particles.

The amount of the at least one optional insect control agent added to the spore-forming bacterium can vary depending on the final formulation as well as the size of the plant and seed to be treated. Preferably, the at least one insect control agent is about 1% by weight of total formulation to about 80% by weight of total formulation. More preferably, the insect control agent is present in an amount of about 5% by weight of total formulation to about 60% by weight of total formulation. Most preferably, the insect control agent is present in an amount of about 10% by weight of total formulation to about 50% by weight of total formulation.

In a further embodiment, the spore-forming bacterium, alone or in combination with the insect control agent, can further comprise an effective amount of at least one fungicide. Preferred fungicides include aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, boscalid, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, dimoxystrobin, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, prothiocinazole, pyraclostrobin, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole, uniconazole, validamycin A, vinclozolin, viniconazole, zarilamide, zineb, ziram and also Dagger G, OK-8705, OK-8801, α-(1,1-dimethylethyl)-β-(2-phenoxyethyl)-1H-1,2,4-triazole-1-ethanol, α-(2,4-dichlorophenyl)-β-fluoro-β-propyl-1H-1,2,4-triazole-1-ethanol, α-(2,4-dichlorophenyl)-β-methoxy-α- methyl-1H-1,2,4-triazole-1-ethanol, α-(5-methyl-1,3-dioxan-5-yl)-β[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-isopropyl{2-methyl-1-[[[1-(4-methylphenyl)-ethyl]-amino]-carbonyl]-propyl}carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidindione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-α-D-glucopyranosyl]amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4,5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl [(4-chlorophenyl)-azo]-cyanoacetate, potassium bicarbonate, methanetetrathiol-sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxy)-3-pyridinyl)-cyclopropanecarboxamide, N-[2,2,2-trichloro-1-[(chloroacetyl)-amino]-ethyl]-benzamide, N-[3-chloro-4,5-bis(2-propinyloxy)-phenyl]-N'-methoxy-methanimidamide, N-formyl-N-hydroxy-DL-alanine-sodium salt, O,O-diethyl [2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, and spiro[2H]-1-benzopyrane-2,1'(3'H)-isobenzofuran]-3'-one, alone or in combination.

The methods disclosed herein have been found to provide a greater degree of plant vigor and yield in nematode infested environments than would be expected from the application of insecticides alone to genetically modified seeds, plants, or plant parts. Various additives, such as fungicides, insecticides, stabilizers, emulsifiers, may be applied to the genetically modified seed or plant depending on the desired properties.

The methods include applying at least one spore-forming bacterium combined with an optional insect control agent, and optional fungicide control agent, to a genetically modified seed, plant, or plant part. Preferably, the spore-forming bacterium is in solution form, emulsifiable concentrate, wettable powders, suspension concentrate, soluble powders, granules, suspension-emulsion concentrate, natural and synthetic materials impregnated with active compound, and fine control release capsules in polymeric substances. Preferably, the insect control agent, if present, is mixed with the spore forming bacterium, and applied simultaneously with the spore forming bacterium. Optionally, the insect control agent can be applied separately to the seed, plant, or plant part. Further, if a fungicide control agent is present, this may be combined with the spore-forming bacterium/insect control agent, or applied separately. If the spore-forming bacterium and insect control agent are in powder form, they may be applied directly to the soil, seed, or foliar separately or mixed together at the time of use. If in liquid form, the spore-forming bacterium and insect control agent, may be sprayed or atomized foliarly or in-furrow at the time of planting, either separately or mixed together at the time of treating. Alternatively, the liquid combination can be introduced to the soil before germination of the seed or directly to the soil in contact with the roots by utilizing a variety of techniques included, but not limited to, drip irrigation, sprinklers, soil injection or soil drenching. Preferably, the liquid is applied to the seed before planting.

Depending on the final formulation and method of application, one or more suitable additives can also be introduced to the spore-forming bacterium and combinations thereof. Additives such as carboxymethylcellulose and natural and synthetic polymers in the form of powders, granules, or latexes, such as gum Arabic, chitin, polyvinyl alcohol and polyvinyl acetate, as well as natural phospholipids, such as cephalins and lecithins, and synthetic phospholipids, can be added to the present compositions.

In a preferred embodiment, the spore-forming bacterium, optional insect control agent, and optional fungicide control agent, are formulated in a single, stable solution, or emulsion or suspension. For solutions, the active chemical compounds (insect control agents and optional fungicide control agent) are dissolved in solvents before adding the spore-forming bacterium. Suitable liquid solvents include petroleum based aromatics, such as xylene, toluene, or alkylnaphthalenes, aliphatic hydrocarbons, such as cyclohexane or paraffins, for example petroleum fractions, mineral and vegetable oils, alcohols, such as butanol or glycol as well as their ethers and esters, ketones, such as methyl ethyl ketone, methyl isobutyl ketone or cyclohexanone, strongly polar solvents, such as dimethylformamide and dimethyl sulphoxide. For emulsions and suspensions, the liquid medium or solvent is water. The spore-forming bacterium, optional insect control agent, and optional fungicide control agent may be suspended in separate liquids and mixed at the time of application. Preferably, the spore forming bacterium, optional insect control agent, and optional fungicide control agent, are combined in a ready to use formulation that exhibits a shelf-life of preferably two years. In use, the liquid can be sprayed or atomized foliarly or in-furrow at the time of planting the corp. The liquid composition can be introduced to the soil before germination of the seed or directly to the soil in contact with the roots by utilizing a variety of techniques including, but not limited to, drip irrigation, sprinklers, soil injection or soil drenching.

Optionally, stabilizers and buffers can be added, including alkaline and alkaline earth metal salts and organic acids, such as citric acid and ascorbic acid, inorganic acids, such as hydrochloric acid or sulfuring acid. Biocides can also be added and can included formaldehydes or formaldehyde-releasing agents and derivatives of benzoic acid, such as p-hydroxybenzoic acid. Further additives include functional agents capable of protecting seeds from harmful effects of selective herbicides such as activated carbon, nutrients (fertilizers), and other agents capable of improving the germination and quality of the products or a combination thereof.

Preferably, the spore-forming bacterium and optional insect control agents are formulated as a liquid seed treatment. The seed treatment comprises at least one spore forming bacterium, and at least one optional insect control agent. Optionally, a fungicide control agent can be mixed with the spore-forming bacterium and insect control agent. The seeds are substantially uniformly coated with one or more layers of spore-forming bacterium, optional insect control agent, and optional fungicide control agent, using conventional methods of mixing, spraying or a combination thereof. Application is done using specifically designed and manufactured equipment that accurately, safely, and efficiently applies seed treatment products to seeds. Such equipment uses various types of coating technology such as rotary coaters, drum coaters, fluidized bed techniques, spouted beds, rotary mists or a combination thereof. Preferably, the application is done via either a spinning "atomizer" disk or a spray nozzle which evenly distributes the seed treatment onto the seed as it moves through the spray pattern. Preferably, the seed is then mixed or tumbled for an additional period of time to achieve additional treatment distribution and drying. The seeds can be primed or unprimed before coating with the inventive compositions to increase the uniformity of germination and emergence. In an alternative embodiment, a dry powder composition can be metered onto the moving seed.

The seeds may be coated via a continuous or batch coating process. In a continuous coating process, continuous flow equipment simultaneously meters both the seed flow and the seed treatment products. A slide gate, cone and orifice, seed wheel, or weight device (belt or diverter) regulates seed flow. Once the seed flow rate through treating equipment is determined, the flow rate of the seed treatment is calibrated to the seed flow rate in order to deliver the desired dose to the seed as it flows through the seed treating equipment. Additionally, a computer system may monitor the seed input to the coating machine, thereby maintaining a constant flow of the appropriate amount of seed.

In a batch coating process, batch treating equipment weighs out a prescribed amount of seed and places the seed into a closed treating chamber or bowl where the corresponding of seed treatment is then applied. The seed and seed treatment are then mixed to achieve a substantially uniform coating on each seed. This batch is then dumped out of the treating chamber in preparation for the treatment of the next batch. With computer control systems, this batch process is automated enabling it to continuously repeat the batch treating process.

In either coating process, the seed coating machinery can optionally be operated by a programmable logic controller that allows various equipment to be started and stopped without employee intervention. The components of this system are commercially available through several sources such as Gustafson Equipment of Shakopee, Minn.

A variety of additives can be added to the seed treatments. Binders can be added and include those composed preferably of an adhesive polymer that can be natural or synthetic without phytotoxic effect on the seed to be coated. A variety of colorants may be employed, including organic chromophores classified as nitroso, nitro, azo, including monoazo, bisazo, and polyazo, diphenylmethane, triarylmethane, xanthene, methane, acridine, thiazole, thiazine, indamine, indophenol, azine, oxazine, anthraquinone, and phthalocyanine. Other additives that can be added include trace nutrients such as salts of iron, manganese, boron, copper, cobalt, molybdenum, and zinc. A polymer or other dust control agent can be applied to retain the treatment on the seed surface.

Other conventional seed treatment additives include, but are not limited to, coating agents, wetting agents, buffering agents, and polysaccharides. At least one agriculturally acceptable carrier can be added to the seed treatment formulation such as water, solids or dry powders. The dry powders can be derived from a variety of materials such as wood barks, calcium carbonate, gypsum, vermiculite, talc, humus, activated charcoal, and various phosphorous compounds.

In one embodiment, the seed coating can comprise of at least one filler, which is an organic or inorganic, natural or synthetic component with which the active components are combined to facilitate its application onto the seed. Preferably, the filler is an inert solid such as clays, natural or synthetic silicates, silica, resins, waxes, solid fertilizers (for example ammonium salts), natural soil minerals, such as kaolins, clays, talc, lime, quartz, attapulgite, montmorillonite, bentonite, or diatomaceous earths, or synthetic minerals, such as silica, alumina, or silicates, in particular aluminum or magnesium silicates.

The spore-forming bacterium, optional insect control agent and optional fungicide control agent, can be combined with any genetically modified plant seed capable of germinating to form a plant or plant part that is susceptible to attack by nematodes and/or pathogenic fungi or bacteria. The genetically modified seed can be any seed that results in a genetically modified plant or plant part that expresses insect toxins or herbicide resistance. Further, the genetically modified seed can be any seed that results in a genetically modified plant or plant part that expresses toxins or resistance to bacterial and fungi. Moreover, the genetically modified seed may be any seed that results in a genetically modified plant or plant part that expresses tolerance to environmental factors such as water stress and nitrogen production. Suitable genetically modified seeds include those of cole crops, vegetables, fruits, trees, fiber crops, oil crops, tuber crops, coffee, flowers, legume, cereals, as well as other plants of the monocotyledonous and dicotyledonous species. Preferably, the genetically modified seeds include peanut, tobacco, grasses, wheat, barley, rye, sorghum, rice, rapeseed, sugarbeet, sunflower, tomato, pepper, bean, lettuce, potato, and carrot. Most preferably, the genetically modified seeds include cotton, soybean, and corn (sweet, field, seed, or popcorn). Particularly preferred genetically modified seeds include DELTA AND PINE LAND® glyphosate tolerant and insect tolerant cotton seeds from Monsanto; STONEVILLE™ glyphosate tolerant and insect tolerant cotton seeds from Bayer CropScience; FIBERMAX® glyphosate tolerant and insect tolerant cotton seeds from Bayer CropScience; glyphosate tolerante soybeans from Stine Seed Company; ASGROW® glyphosate tolerant soybean seeds from Monsanto; PIONEER® glyphosate tolerant and insect tolerant corn seeds from DuPont; NORTHRUP KING™ glyphosate tolerant soybean seeds from Syngenta; glyphosate tolerant and insect tolerant corn seeds from Burrus Company; and Garst Company (AGRIEDGE™) glyphosate tolerant and insect tolerant corn seeds from Syngenta.

Advantages of the novel combination of spore-forming bacterium and genetically modified seed will be apparent from the non-limiting examples below. The following examples demonstrate unexpected improvements in overall plant crop yield by combining the spore-forming bacterium with an insect control agent and applying the combination to genetically modified seeds.

EXAMPLES

Example 1

Example 1 shows the crop yield results under nematode pressure for the combination of spore-forming bacterium and insect control agent applied to genetically modified seed (control+spore forming bacterium) compared to genetically modified seed with just an insect control agent (control). The genetically modified seeds in this comparison experiment were sourced from DELTA AND PINE LAND® available from Monsanto, which are cotton seeds that contains both glyphosate tolerance (Round-up Ready® trait) and insect tolerance (Bt gene) gene expressions. The insecticide was imidacloprid (Gaucho Grande) or imidacloprid & thiodicarb (AERIS®). The spore-forming bacterium was *B. firmus*. The nematode type varied from none, root knot nematode, reiniform nematode, and lance nematode. The concentration of insect control agents was 600 gm ai/liter, and in liquid form. The application rate of the insect control agents was 500-1000 gm ai/100 kg. The concentration of *B. firmus* ranged from 100,000 to 10,000,000 colony forming units per seed. The insect control agent and *B. firmus* were mixed together in an aqueous suspension in enough volume to adequately cover the cottonseed. The rate of the mixture varied from 1369-2608 ml per 100 kg of seed to assure adequate coverage of the various seed sizes. Once planted, the cotton seed grew to full maturity and the results measured in pounds of cotton per acre. The below table compares the pounds of cotton per acre between the control and the control plus spore forming bacterium at various nematode types. The yield difference numbers represent an average of several experimental results, unless otherwise indicated.

| Exp. No. | Nematode | Control | Control + *B. firmus* | Yield difference |
|---|---|---|---|---|
| 1 | Lance | 2957 | 3206 | 249 |
| 2 | Reniform | 2044 | 2132 | 88 |
| 3 | Root Knot | 2183 | 2111 | −72 |
| 4 | Root Knot | 3226 | 3298 | 72 |
| 5 | Root Knot | 3064 | 3254 | 190 |
| 6 | Root Knot | 337 | 300 | −37 |
| 7 | Root Knot | 1530 | 1643 | 113 |
| 8 | Reniform | 1165 | 1165 | 0 |
| 9 | None | 2280 | 2250 | −30 |
| 10 | None | 2108 | 2230 | 122 |
| 11 | Reniform | 2645 | 2721 | 76 |
| 12 | Root Knot | 1884 | 1799 | −85 |
| 13 | None | 3007 | 3246 | 239 |
| 14 | Root Knot | 1615 | 1602 | −13 |

Some of the negative yield values are the result of uncontrollable environmental and planting issues. Regarding Experiment Number 3, the negative value may be attributable to low planting numbers from planter error, which will effect overall crop yield. For Experiment No. 6, no replicates were done because of damage to the planting plots.

Example 2

Example 2 shows the crop yield results under nematode pressure for the combination of spore-forming bacterium and insect control agent applied to genetically modified seed (control+spore forming bacterium) compared to genetically modified seed with just an insect control agent (control). The genetically modified seed in this comparison experiment were sourced from STONEVILLE™ available from Bayer CropScience, which are cotton seeds that contain both glyphosate tolerance (ROUND-UP READY® trait) and insect tolerance (Bt gene) gene expressions. The insecticide was imidacloprid (GAUCHO GRANDE®) or imidacloprid & thiodicarb (AERIS®). The spore-forming bacterium was *B. firmus*. The nematode type varied from none, root knot nematode and reniform nematode. The concentration of insect control agents was 600 gm ai/liter, and in liquid form. The application rate of the insect control agents was 500-1000 gm ai/100 kg. The concentration of *B. firmus* ranged from 100,000 to 10,000,000 colony forming units per seed. The insect control agent and *B. firmus* were mixed together in an aqueous suspension in enough volume to adequately cover the cottonseed. The rate of the mixture varied from 1369-2608 ml per 100 kg of seed to assure adequate coverage of the various seed sizes. Once planted, the cotton seed grew to full maturity and the results measured in pounds of cotton per acre. The below table compares the pounds of cotton per acre between the control and the control plus spore forming bacterium at various nematode types. The yield difference numbers represent an average of several experimental results, unless otherwise indicated.

| Exp. No. | Nematode | Control | Control + *B. firmus* | Yield difference |
|---|---|---|---|---|
| 1 | Root Knot | 1658 | 1728 | 70 |
| 2 | Root Knot | 2780 | 2766 | −14 |
| 3 | Reniform | 404 | 377 | −27 |
| 4 | None | 596 | 632 | 36 |

Example 3

Example 3 shows the crop yield results under nematode pressure for the combination of spore-forming bacterium and insect control agent applied to genetically modified seed (control+spore-forming bacterium) compared to genetically modified seed with just an insect control agent (control). The genetically modified seed in this comparison experiment were sourced from FIBERMAX® available from Bayer CropScience, which are cotton seeds that contains both glyphosate tolerance (ROUND-UP READY® trait) and insect tolerance (Bt gene) gene expressions. The insecticide was imidacloprid (GAUCHO GRANDE®) or imidacloprid & thiodicarb (AERIS®). The spore-forming bacterium was *B. firmus*. The nematode types were root knot nematode and reniform nematode. The concentration of insect control agents was 600 gm ai/liter, and in liquid form. The concentration of *B. firmus* ranged from 100,000 to 10,000,000 colony forming units per seed. The insect control agent and *B. firmus* were mixed together in an aqueous suspension in enough volume to adequately cover the cotton seed. The rate of the mixture varied from 1369-2608 ml per 100 kg of seed to assure adequate coverage of the various seed sizes. Once planted, the cotton seed grew to full maturity and the results measured in pounds of cotton per acre. The below table compares the pounds of cotton per acre between the control and the control plus spore-forming bacterium at various nematode types. The yield difference numbers represent an average of several experimental results, unless otherwise indicated.

| Exp. No. | Nematode | Control | Control + *B. firmus* | Yield difference |
| --- | --- | --- | --- | --- |
| 1 | Root Knot | 1541 | 1589 | 48 |
| 2 | Reniform | 313 | 327 | 14 |
| 3 | Root Knot | 1105 | 1236 | 131 |

Example 4

Example 4 shows the crop yield results under nematode pressure for the combination of spore-forming bacterium and insect control agent applied to genetically modified seed (control+spore forming bacterium) compared to genetically modified seed with just an insect control agent (control). The genetically modified seed in this comparison experiment are from Stine Seed Company, which are soybean seeds that contain glyphosate tolerance (ROUND-UP READY® trait) gene expression. The insecticide was imidacloprid (GAUCHO®). The spore-forming bacterium was *B. firmus*. The nematode types were none, root knot nematode, and soybean cyst. The concentration of insect control agents was 600 gm ai/liter, and was in liquid form. The concentration of *B. firmus* ranged from 100,000 to 10,000,000 colony forming units per seed. The insect control agent and *B. firmus* were mixed together in an aqueous suspension in enough volume to adequately cover the soybean seed. The rate of the mixture varied from 261-652 ml per 100 kg of seed to assure adequate coverage of the various seed sizes. Once planted, the soybean seed grew to full maturity and the results measured in bushels of soybean per acre. The below table compares the bushels of soybean per acre between the control and the control plus spore forming bacterium at various nematode types. The yield difference numbers represent an average of several experimental results, unless otherwise indicated.

| Exp. No. | Nematode | Control | Control + *B. firmus* | Yield difference |
| --- | --- | --- | --- | --- |
| 1 | None | 64.4 | 63.4 | -1 |
| 2 | Soybean Cyst | 42.8 | 44 | 1.2 |
| 3 | Soybean Cyst | 36.1 | 39.5 | 3.4 |
| 4 | Soybean Cyst | 41 | 45 | 4 |
| 5 | Soybean Cyst | 68 | 67 | -1 |
| 6 | None | 59.7 | 55.3 | -4.4 |
| 7 | Root Knot | 29.9 | 31.7 | 1.8 |
| 8 | None | 53 | 53.3 | 0.3 |

Example 5

Example 5 shows the crop yield results under nematode pressure for the combination of spore-forming bacterium and insect control agent applied to genetically modified seed (control+spore-forming bacterium) compared to genetically modified seed with just an insect control agent (control). The genetically modified seed in this comparison experiment was ASGROW® from Monsanto, which is a soybean seed that contains glyphosate tolerance (ROUND-UP READY® trait) gene expression. The insecticide was imidacloprid (GAUCHO®). The spore-forming bacterium was *B. firmus*. The nematode types were root knot nematode and soybean cyst. The concentration of insect control agent was 600 gm ai/liter and were in liquid form. The concentration of *B. firmus* ranged from 100,000 to 10,000,000 colony forming units per seed. The insect control agent and *B. firmus* were mixed together in an aqueous suspension in enough volume to adequately cover the soybean seed. The rate of the mixture varied from 261-652 ml per 100 kg of seed to assure adequate coverage of the various seed sizes. Once planted, the soybean seed grew to full maturity and the results measured in bushels of soybean per acre. The below table compares the bushels of soybean per acre between the control and the control plus spore forming bacterium. The yield difference numbers represent an average of several experimental results, unless otherwise indicated.

| Exp. No. | Nematode | Control | Control + *B. firmus* | Yield difference |
| --- | --- | --- | --- | --- |
| 1 | Root Knot and Soybean Cyst | 25.4 | 26.9 | 1.5 |

Example 6

Example 6 shows the crop yield results under nematode pressure for the combination of spore-forming bacterium and insect control agent applied to genetically modified seed (control+spore-forming bacterium) compared to genetically modified seed with just an insect control agent (control). The genetically modified seed in this comparison experiment were sourced from PIONEER® from DuPont, which are soybean seeds that contain glyphosate tolerance (ROUND-UP READY® trait) gene expression. The insecticide was imidacloprid (GAUCHO®). The spore-forming bacterium was *B. firmus*. The nematode types were none and soybean cyst. The concentration of insect control agent was 600 gm ai/liter, and were in liquid form. The concentration of *B. firmus* ranged from 100,000 to 10,000,000 colony forming units per seed. The insect control agent and *B. firmus* were mixed together in an aqueous suspension in enough volume to adequately cover the soybean seed. The rate of the mixture varied from 261-652 ml per 100 kg of seed to assure adequate coverage of the various seed sizes. Once planted, the soybean seed grew to full maturity and the results measured in bushels of soybean per acre. The below table compares the bushels of soybean per acre between the control and the control plus spore-forming bacterium. The yield difference numbers represent an average of several experimental results, unless otherwise indicated.

| Exp. No. | Nematode | Control | Control + *B. firmus* | Yield difference |
| --- | --- | --- | --- | --- |
| 1 | None | 61 | 62.6 | 1.6 |
| 2 | Soybean Cyst | 27.2 | 28.3 | 1.1 |
| 3 | Soybean Cyst | 29.9 | 31.7 | 1.8 |

Example 7

Example 7 shows the crop yield results under nematode pressure for the combination of spore-forming bacterium and insect control agent applied to genetically modified seed (control+spore-forming bacterium) compared to genetically modified seed with just an insect control agent (control). The genetically modified seed in this comparison experiment was sourced from NORTHRUP KING™ of Syngenta Seeds, which is a soybean seed that contains glyphosate tolerance (ROUND-UP READY® trait) gene expression. The insecticide was imidacloprid (GAUCHO®). The spore-forming bacterium was *B. firmus*. The nematode type was soybean cyst. The concentration of insect control agent was 600 gm ai/liter, and was in liquid form. The concentration of *B. firmus* ranged from 100,000 to 10,000,000 colony forming units per seed. The insect control agent and *B. firmus* were mixed together in an aqueous suspension in enough volume to adequately cover the soybean seed. The rate of mixture seed coverage varied from 261-652 ml per 100 kg of seed. Once planted, the soybean seed grew to full maturity and the results measured in bushels of soybean per acre. The below table compares the bushels of soybean per acre between the control and the control plus spore forming bacterium. The yield difference numbers represent an average of several experimental results, unless otherwise indicated.

| Exp. No. | Nematode | Control | Control + *B. firmus* | Yield difference |
|---|---|---|---|---|
| 1 | Soybean Cyst | 44 | 45.3 | 1.3 |
| 2 | Soybean Cyst | 46 | 46.3 | 0.3 |

Example 8

Example 8 shows the crop yield results under nematode pressure for the combination of spore-forming bacterium and insect control agent applied to genetically modified seed (control+spore-forming bacterium) compared to genetically modified seed with just an insect control agent (control). The genetically modified seed in this comparison experiment was sourced from PIONEER® from DuPont, which is a corn seed that contains both glyphosate tolerance (ROUND-UP READY® trait) and insect tolerance (Bt gene) gene expressions. The insecticide was clothianidin (PONCHO®). The spore-forming bacterium was *B. firmus*. Multiple species of nematodes were present. The concentration of insect control agent was 600 gm ai/liter, and was in liquid form. The concentration of *B. firmus* ranged from 100,000 to 10,000,000 colony forming units per seed. The insect control agent and *B. firmus* were mixed together in an aqueous suspension in enough volume to adequately cover the corn seed. The rate of the mixture varied from 522-1044 ml per 100 kg of seed to assure adequate coverage of the various seed sizes. Once planted, the corn seed grew to full maturity and the results measured in bushels of corn per acre. The below table compares the bushels of corn per acre between the control and the control plus spore forming bacterium. The yield difference numbers represent an average of several experimental results, unless otherwise indicated.

| Exp. No. | Nematode | Control | Control + *B. firmus* | Yield difference |
|---|---|---|---|---|
| 1 | Multiple species | 119.3 | 132.3 | 13 |

Example 9

Example 9 shows the crop yield results under nematode pressure for the combination of spore-forming bacterium and insect control agent applied to genetically modified seed (control+spore-forming bacterium) compared to genetically modified seed with just an insect control agent (control). The genetically modified seeds in this comparison experiment were sourced from Burrus Company, which are corn seeds that contains both glyphosate tolerance (ROUND-UP READY® trait) and insect tolerance (varies) gene expressions. The insecticide was clothianidin (PONCHO®). The spore-forming bacterium was *B. firmus*. Multiple species of nematodes were present. The concentration of insect control agent was 600 gm ai/liter, and in liquid form. The concentration of *B. firmus* ranged from 100,000 to 10,000,000 colony forming units per seed. The insect control agent and *B. firmus* were mixed together in an aqueous suspension in enough volume to adequately cover the corn seed. The rate of the mixture varied from 522-1044 ml per 100 kg of seed to assure adequate coverage of the various seed sizes. Once planted, the corn seed grew to full maturity and the results measured in bushels of corn per acre. The below table compares the bushels of corn per acre between the control and the control plus spore-forming bacterium. The yield difference numbers represent an average of several experimental results, unless otherwise indicated.

| Exp. No. | Nematode | Insect tolerance gene | Control | Control + *B. firmus* | Yield difference |
|---|---|---|---|---|---|
| 1 | Multiple species | Corn root worm and Bt | 148.1 | 146.8 | −1.3 |
| 2 | Multiple species | Bt | 172 | 183.5 | 11.5 |

Example 10

Example 10 shows the crop yield results under nematode pressure for the combination of spore-forming bacterium and insect control agent applied to genetically modified seed (control+spore-forming bacterium) compared to genetically modified seed with just an insect control agent (control). The genetically modified seed in this comparison experiment was sourced from Garst Company (AGRIEDGE™) of Syngenta Seeds, which is a corn seed that contains both glyphosate tolerance (ROUND-UP READY® trait) and insect tolerance (corn root worm) gene expressions. The insecticide was clothianidin (PONCHO®). The spore-forming bacterium was *B. firmus*. Multiple species of nematodes were present. The concentration of insect control agent was 600 gm ai/liter, and in liquid form. The concentration of *B. firmus* ranged from 100,000 to 10,000,000 colony forming units per seed. The insect control agent and *B. firmus* were mixed together in an aqueous suspension in enough volume to adequately cover the corn seed. The rate of the mixture varied from 522-1044 ml per 100 kg of seed to assure adequate coverage of the various seed sizes. Once planted, the corn seed grew to full maturity and the results measured in bushels of corn per acre. The below table compares the bushels of corn per acre between the control and the control plus spore-forming bacterium. The yield difference numbers represent an average of several experimental results, unless otherwise indicated.

| Exp. No. | Nematode | Control | Control + *B. firmus* | Yield difference |
|---|---|---|---|---|
| 1 | Multiple species | 170.12 | 163.3 | −6.82 |
| 2 | Multiple species | 136 | 133.1 | −2.9 |

The negative yield difference values for each experiment are most likely attributable to damages planting plots, which resulted in no replicate experiments. When averaging Experiment Number 1 and 2, the Control is 142.6, the Control+*B. firmus* is 146.1, and the Yield difference is 3.5. Therefore, the use of the spore-forming bacterium shows a net positive result.

Example 11

Example 11 shows the crop yield results under nematode pressure for the combination of spore-forming bacterium and insect control agent applied to genetically modified seed (control+spore-forming bacterium) compared to genetically modified seed with just an insect control agent (control). The genetically modified seed in this comparison experiment was an unknown corn seed purchased from a production company that contains various gene expressions for both herbicide resistance and insect resistance. The insecticide was clothianidin (PONCHO®). The spore-forming bacterium was *B. firmus*. Multiple species of nematodes were present. The concentration of insect control agent was 600 gm ai/liter, and in liquid form. The concentration of *B. firmus* ranged from 100,000 to 10,000,000 colony forming units per seed. The insect control agent and *B. firmus* were mixed together in an aqueous suspension in enough volume to adequately cover the corn seed. The rate of the mixture varied from 522-1044 ml per 100 kg of seed to assure adequate coverage of the various seed sizes. Once planted, the corn seed grew to full maturity and the results measured in bushels of corn per acre. The below table compares the bushels of corn per acre between the control and the control plus spore-forming bacterium. The yield difference numbers represent an average of several experimental results, unless otherwise indicated.

| Exp. No. | Nematode | Gene Expression | Control | Control + B. firmus | Yield difference |
|---|---|---|---|---|---|
| 1 | Multiple species | Bt and corn borer | 131.7 | 146 | 14.3 |
| 2 | Multiple species | Bt and Hurculex | 194.8 | 200.5 | 5.7 |
| 3 | Multiple species | Bt and Hurculex | 204.2 | 227.6 | 23.4 |

The results above are surprising. As shown above, most seed varieties faired better with the combination of spore-forming bacterium and insect control agent verses just the insect control agent.

According to some embodiments, the following percent crop yield increases were obtained. Regarding soybean seed, the addition of spore-forming bacterium to NORTHUP KING™ soybean seed, PIONEER® soybean seed, and soybean seed from Stine Seed Company showed about a 2% increase, 5%-10% increase, and 4.3% increase, respectively, in soybean bushel yield. This improvement, spread out over several hundred acres results in a significant improvement in crop yield. Regarding cotton seed, the addition of spore-forming bacterium to DELTA AND PINE LAND® cotton seed and FIBERMAX® cotton seed showed about a 3% increase and 6.5% increase, respectively, in pounds of cotton per acre. Again, spreading this improvement over several hundred acres of cotton plant yields a drastic improvement in yield. Regarding corn seed, the addition of spore-forming bacterium to corn seed from Burrus Seed Company and unknown commercially available corn seed showed about a 3.2% increase and 8% increase, respectively, in bushels of corn per acre. Again, this results in a huge improvement in overall crop yield when spread out over several hundred acres. Overall, there is a surprising advantage in crop yield when using the combination of spore-forming bacterium and insect control agent with genetically modified seeds.

Additional advantages, features and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

All documents referred to herein are specifically incorporated herein by reference in their entireties.

As used herein and in the following claims, articles such as "the", "a" and "an" can connote the singular or plural.

What is claimed is:

1. A product comprising:
   at least one spore-forming bacterium;
   at least one insect control agent; and
   at least one genetically modified cotton, corn, or soybean seed,
   wherein the insect control agent, comprises 1-(2-chloro-1,3-thiazol-5-ylmethyl)-3-methyl-2-nitroguanidine (clothianidin),
   wherein the at least one spore-forming bacterium exhibits nematicidal activity and is *Bacillus firmus* from strain CNCM I-1582, and
   wherein the genetically modified seed is insect tolerant, glyphosate tolerant, or a combination thereof.

2. The product of claim 1, wherein said genetically modified seed is transformed with a gene from *B. thuringiensis*.

3. The product of claim 1, wherein said genetically modified seed is selected from the group consisting of: glyphosate tolerant and insect tolerant cotton seeds; glyphosate tolerant soybean seeds; and glyphosate tolerant and insect tolerant corn seeds.

4. The product of claim 1, further comprising at least one chemical fungicide.

5. A method of protecting a genetically modified cotton, corn, or soybean seed from nematodes, comprising applying to the seed at least one spore-forming bacterium; and at least one insect control agent,
   wherein the insect control agent comprises 1-(2-chloro-1,3-thiazol-5-ylmethyl)-3-methyl-2-nitroguanidine (clothianidin),
   wherein the at least one spore-forming bacterium exhibits nematicidal activity and is *Bacillus firmus* from strain CNCM I-1582, and
   wherein the genetically modified seed is insect tolerant, glyphosate tolerant, or a combination thereof.

6. The method of claim 5, wherein said spore-forming bacterium and insect control agent are applied simultaneously to said genetically modified seed.

7. The method of claim 5, wherein said genetically modified seed is transformed with a gene from *B. thuringiensis*.

8. A method of protecting a genetically modified cotton, corn, or soybean seed from nematodes comprising providing at least one composition comprising 0.0001 to 20% by weight of at least one spore-forming bacterium and 0.001 to 20% by weight of at least one insect control agent; and applying the composition to the seed,
   wherein the insect control agent comprises 1-(2-chloro-1,3-thiazol-5-ylmethyl)-3-methyl-2-nitroguanidine (clothianidin), wherein the at least one spore-forming bacterium exhibits nematicidal activity and is *Bacillus firmus* from strain CNCM 1-1582, and wherein the genetically modified seed is insect tolerant, glyphosate tolerant, or a combination thereof.

9. The method of claim 8, wherein the composition is applied by a method selected from the group consisting of: drip irrigation, sprinklers, foliar spray, seed coating, soil injection or soil drenching.

10. A composition for protecting a genetically modified cotton, corn, or soybean seed from nematodes comprising: (i) at least one spore-forming bacterium in an amount of from about 2% by weight to 80% by weight; (ii) at least one insect control agent in an amount of from about 1% by weight to about 80% by weight; and (iii) a solvent, wherein the insect control agent comprises 1-(2-chloro-1,3-thiazol-5-ylmethyl)-3-methyl-2-nitroguanidine (clothianidin), wherein the at least one spore-forming bacterium exhibits nematicidal activity and is *Bacillus firmus* from strain CNCM 1-1582, and wherein the genetically modified seed is insect tolerant, glyphosate tolerant, or a combination thereof.

11. A method of manufacturing a genetically modified cotton, corn, or soybean seed treated with at least one spore-forming bacteria and an insect control agent comprising: (i) applying said spore-forming bacteria and optional insect control agent to said genetically modified seed; and (ii) mixing said genetically modified seed to achieve a substantially uniform treatment, wherein the insect control agent comprises 1-(2-chloro-1,3-thiazol-5-ylmethyl)-3-methyl-2-nitroguanidine (clothianidin), wherein the at least one spore-forming bacterium exhibits nematicidal activity and is *Bacillus firmus* from strain CNCM 1-1582, and wherein the genetically modified seed is insect tolerant, glyphosate tolerant, or a combination thereof.

12. The method of claim 11, wherein a continuous coating machine is used to apply said spore-forming bacteria and insect control agent.

13. The method of claim 12, wherein a computer system monitors the flow of genetically modified seed into the continuous coating machine.

14. The method of claim 11, wherein a batch coating process is used to apply said spore-forming bacteria and insect control agent.

15. The method of claim 14, wherein said batch coating process comprises: (i) weighing a set amount of genetically modified seed; (ii) placing the seed into a closed treating chamber; (iii) adding the spore-forming bacteria and insect control agent into the treating chamber; and (iv) mixing said genetically modified seed, spore-forming bacteria, and insect control agent.

16. A genetically modified cotton, corn, or soybean seed coated with at least one spore-forming bacterium and at least one insect control agent, wherein the insect control agent comprises 1-(2-chloro-1,3-thiazol-5-ylmethyl)-3-methyl-2-nitroguanidine (clothianidin), wherein the at least one spore-forming bacterium exhibits nematicidal activity and is *Bacillus firmus* from strain CNCM 1-1582, and wherein the genetically modified seed is insect tolerant, glyphosate tolerant, or a combination thereof.

* * * * *